(12) United States Patent
Waluszko

(10) Patent No.: US 6,911,657 B2
(45) Date of Patent: *Jun. 28, 2005

(54) TRANSILLUMINATOR

(76) Inventor: Alex Waluszko, 1215 Valley View Ave., Pasadena, CA (US) 91107

( * ) Notice: Subject to any disclaimer, the term of this patent is extended or adjusted under 35 U.S.C. 154(b) by 0 days.

This patent is subject to a terminal disclaimer.

(21) Appl. No.: 10/693,071

(22) Filed: Oct. 24, 2003

(65) Prior Publication Data
US 2004/0084630 A1 May 6, 2004

Related U.S. Application Data

(63) Continuation-in-part of application No. 10/015,427, filed on Dec. 12, 2001, now Pat. No. 6,670,619.

(51) Int. Cl.$^7$ .......................... G01N 21/33; G01N 21/00
(52) U.S. Cl. ..................... 250/455.11; 250/504 R; 250/365; 250/372; 250/454.11
(58) Field of Search ................. 250/455.11, 504 R, 250/365, 372, 454.11

(56) References Cited

U.S. PATENT DOCUMENTS

| | | | | |
|---|---|---|---|---|
| 4,983,881 A | * | 1/1991 | Eliasson et al. | 313/607 |
| 5,175,437 A | * | 12/1992 | Waluszko | 250/504 R |
| 6,670,619 B2 | * | 12/2003 | Waluszko | 250/492.1 |

* cited by examiner

Primary Examiner—Nikita Wells

(57) ABSTRACT

An apparatus for expeditiously irradiating an object with ultraviolet radiation at a selected UV wavelength. The apparatus includes a plurality of ultraviolet sources, each emitting radiation at a first wavelength. The UV sources are mounted within a housing that also supports one or more conversion plates that can be interposed between the UV sources and the specimen and function to convert the UV to a second wavelength.

24 Claims, 15 Drawing Sheets

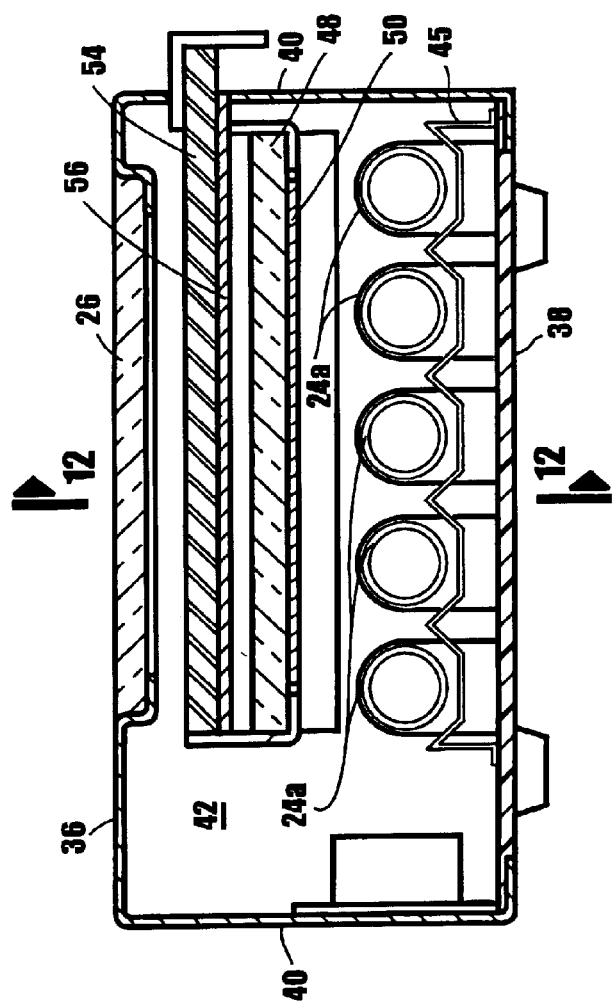
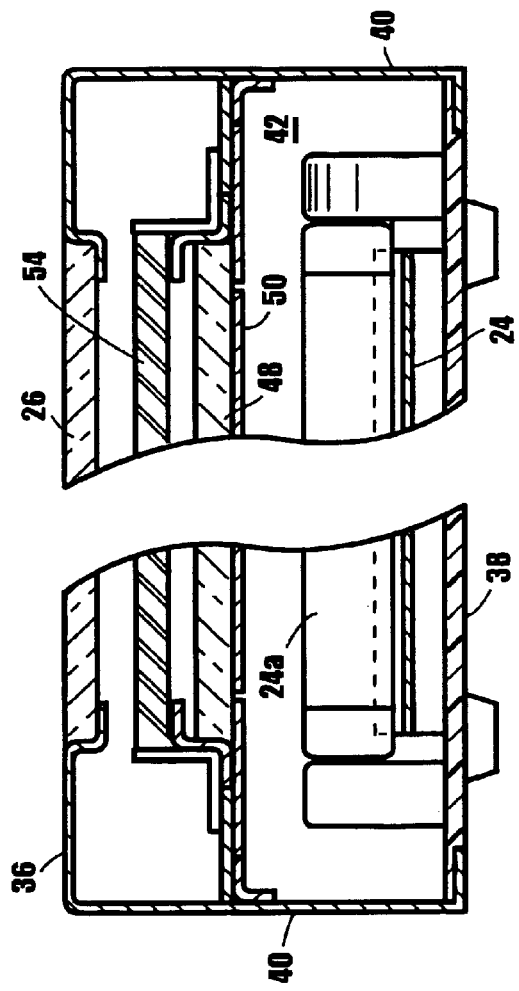
Fig. 11
Fig. 12

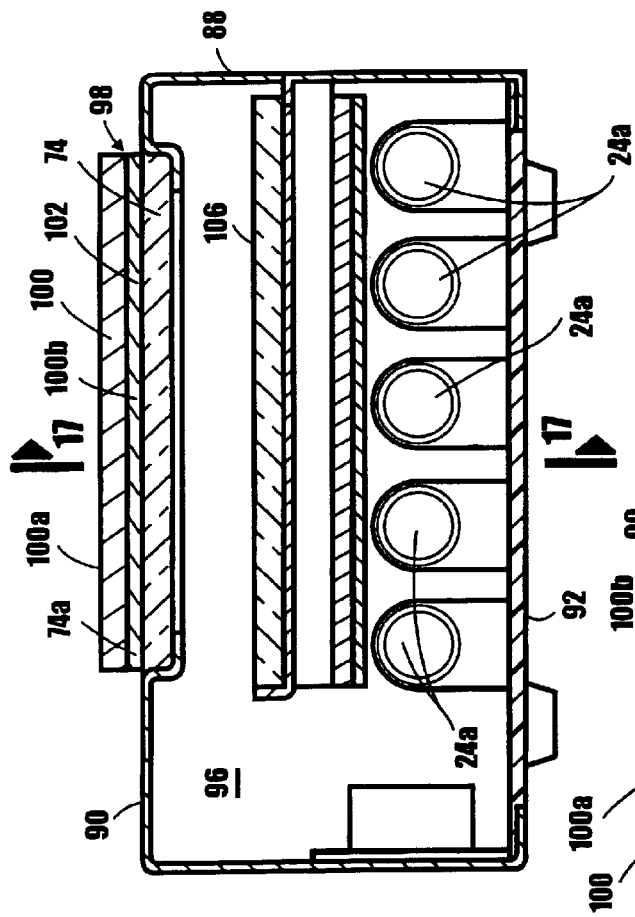
Fig. 16
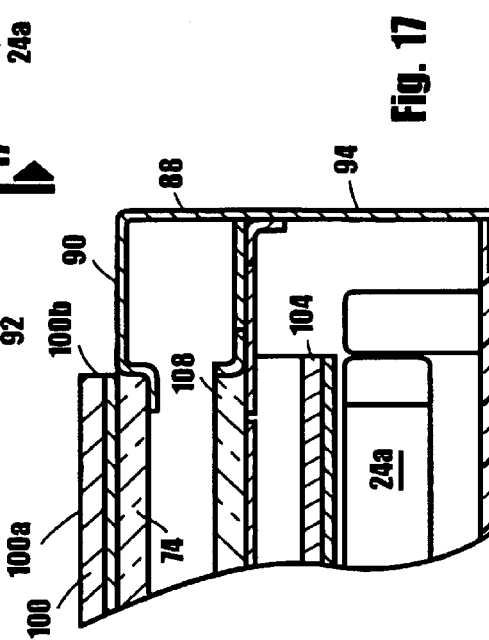
Fig. 17
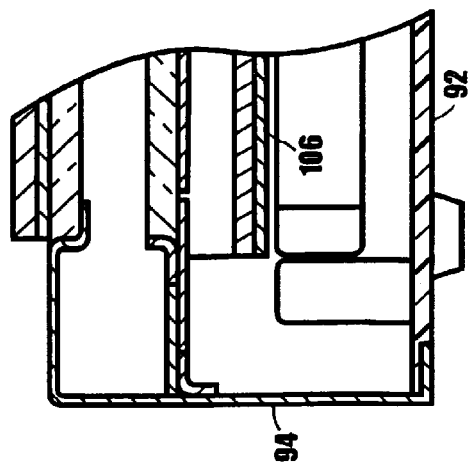

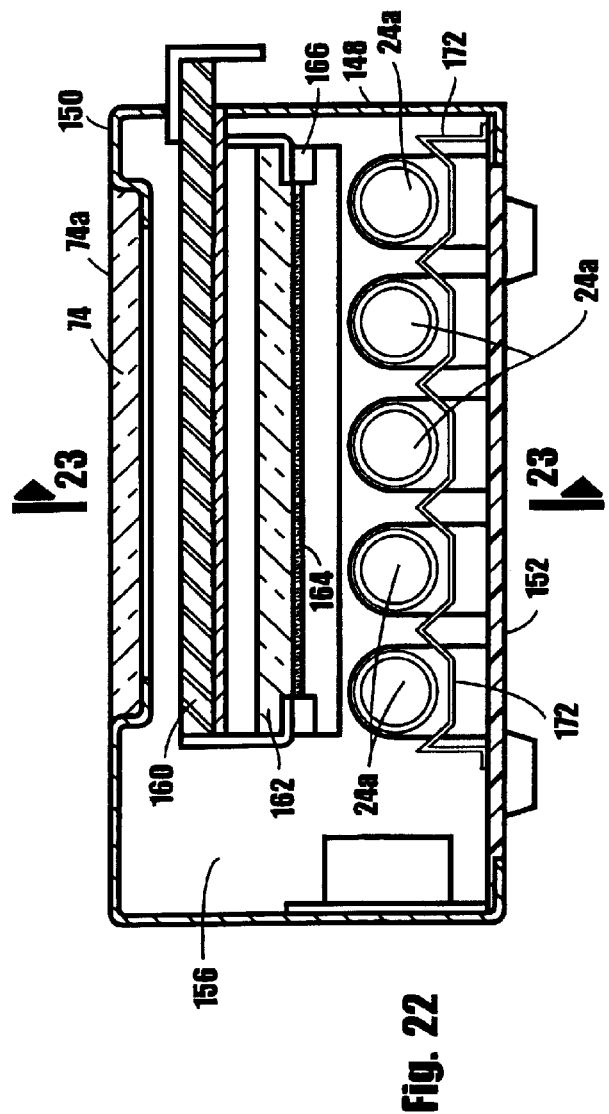
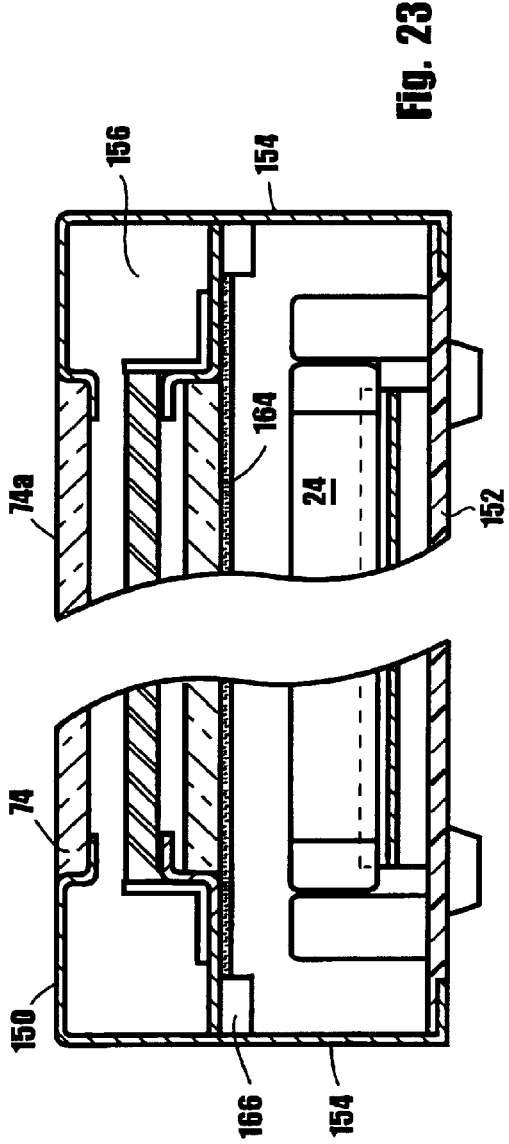
Fig. 22
Fig. 23

TRANSILLUMINATOR

This is a Continuation-In-Part Application of U.S. application Ser. No. 10/015,427 filed Dec. 12, 2001 now U.S. Pat. No. 6,670,619.

BACKGROUND OF THE INVENTION

1. Field of the Invention

The present invention relates generally to radiation devices. More particularly, the invention concerns an apparatus for irradiating various articles with ultra-violet radiation from a radiation source such as a plurality of ultra-violet lamps.

2. Discussion of the Prior Art

Ultra-violet radiation is widely used in industry and science for sterilization through inactivation of microorganisms, for inducing and promoting various types of photochemical reactions and for controllably exposing various types of photosensitive materials. By way of example, U.S. Pat. No. 5,175,347 issued to the present inventor describes an apparatus for irradiating an object such as a specimen of material with ultraviolet radiation at a selected long, short or mid-wave length. Similarly, U.S. Pat. No. 3,936,186 issued to Boland et al discloses an apparatus for exposing diazo printing plates and the like of the character that are used in the graphic arts field. In like manner, U.S. Pat. No. 5,288,647 issued Zimlich, Jr. et al relates to a method by which polynucleotide specimens can be irradiated particularly for the purpose of fixing them to a substrate.

Ultraviolet light (UV), which is electromagnetic radiation in the region of the spectrum located between X-rays and visible light, is typically divided into three principal ranges, namely long wave, mid-range, and short wave. For each of these UV ranges specific applications have been developed.

As a general rule, the desired ultraviolet wavelength is obtained from a fluorescent style tube that is an electric discharge device that uses a low-pressure mercury vapor arc to generate ultraviolet energy. The ultraviolet energy released in typical, commercially available fluorescent tubes is primarily at the wavelength of about 254 nanometers. The fluorescent tubes can be modified to release other ultraviolet wavelengths by the use of phosphors, which have the ability to absorb the ultraviolet energy and re-radiate it in other wavelengths. For example, long wave ultraviolet of about 365 nanometers and mid-range ultraviolet of about 300 nanometers are created by coating the inside of the fluorescent tubes with the proper phosphors which convert the short wave ultraviolet.

In the past ultraviolet irradiation of selected articles has been accomplished using single or multiple UV range fluorescent tubes mounted within a suitable enclosure. In order to eliminate white light generated by the UV tube, some prior art devices make use of a UV transmitting, ambient or white or visible light blocking filter that is typically mounted in front of the UV tube.

In the past, when it was desired to obtain two UV wave lengths from the radiation device, two UV tubes emitting two levels of UV radiation were mounted side by side within the device, and an appropriate filter was placed in front of each tube.

In the apparatus disclosed in the previously identified U.S. Pat. No. 5,175,347 issued to the present inventor, a different and novel technique was used to irradiating an object, with ultraviolet radiation at a selected long, short or mid-wave length. More particularly, in this prior art apparatus, a plurality of ultraviolet sources, each emitting radiation at a different wave length, were mounted within a rotatable array so that a selected one of the sources could be moved into alignment with the specimen and automatically energized by merely rotating the array.

As will be better understood from the discussion that follows, the present invention enables the controlled irradiation of a specimen with UV at selected wavelengths through the use of a novel wavelength conversion means that can be interposed between the UV source and the specimen.

SUMMARY OF THE INVENTION

It is an object of the present invention to provide an apparatus for expeditiously irradiating an object with ultraviolet radiation at a selected UV wavelength.

More particularly, the apparatus of the invention comprises a plurality of ultraviolet sources, each emitting radiation at a first wave length. The UV sources are mounted within a housing that also supports a novel conversion plate that can be interposed between the UV sources and the specimen and functions to convert the UV to a second wavelength.

Another object of the invention is to provide an apparatus of the aforementioned character in which the conversion plate is slidably carried by the housing.

Another object of the invention is to provide an apparatus as described in the preceding paragraphs in which the specimen can be irradiated with ultraviolet radiation at a selected wavelength between about 254 nanometers about 312 nanometers and about 365 nanometers as well as combinations of these wavelengths and selected wavelengths from the visible spectrum.

Still another object of the invention is to provide an apparatus of the class described, which includes strategically located reflectors for reflecting the ultraviolet radiation in a direction toward the specimen. Another object of the invention is to provide an apparatus as described in the preceding paragraphs in which a filter for blocking white light from the UV sources is interposed between the specimen and the UV sources.

Another object of this invention is to provide a platform that transmits selected UV visible or infrared wavelengths on which an irradiated sample rests, which is separate from the UV transmitting filter and/or white light blocking filter.

Another object of the invention is to provide an apparatus that will readily convert one UV radiation provided by a conventional UV lamp source into a second UV or combination UV/visible wavelength.

A further object of the invention is to provide in combination a UV transmitting apparatus of the character described herein and a separate UV transparent worksurface.

Yet another object of the invention is to provide an apparatus of the character described which is of a simple, compact construction that is easy to use and can be inexpensively manufactured.

BRIEF DESCRIPTION OF THE DRAWINGS

FIG. 4 is a cross-sectional to take along lines 4—4 FIG. 3.

FIG. 11 is a transverse, cross-sectional view of the form of the apparatus shown in FIG. 10.

FIG. 12 is a cross-sectional view taken along lines 12—12 FIG. 11.

FIG. 16 is a transverse cross-sectional view of still another form of the apparatus of the invention.

FIG. 17 is a cross-sectional view taken along lines 17—17 of FIG. 16.

FIG. 22 is a transverse cross-sectional view of yet another form of the apparatus of the invention.

FIG. 23 is a cross-sectional view taken along lines 23—23 of FIG. 22.

DESCRIPTION OF THE INVENTION

Figure 1:
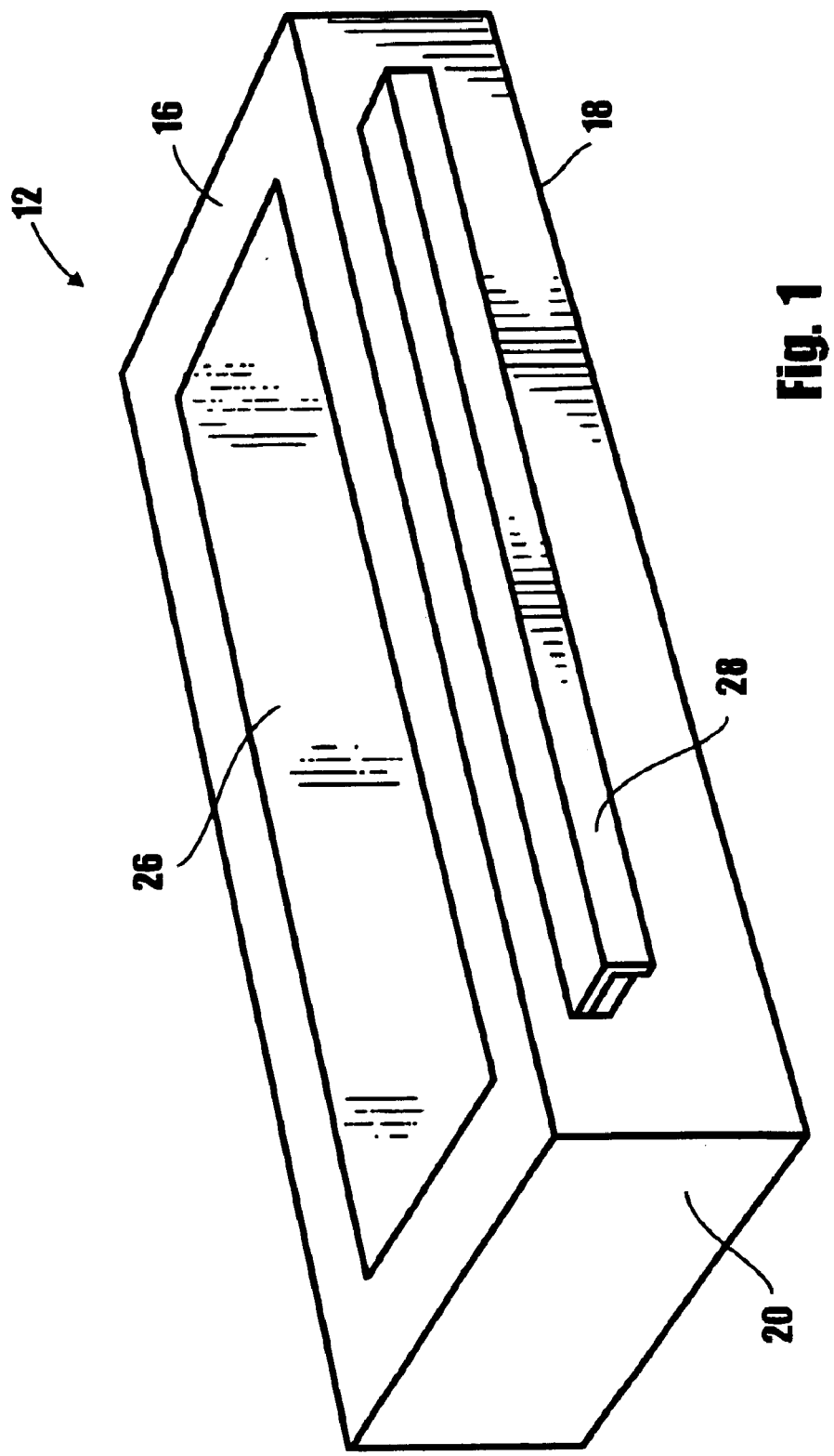
FIG. 1 is a generally perspective view of one form of the apparatus of the invention for irradiating an object with ultraviolet radiation.

Referring to the drawings and particularly to FIGS. 1 through 9, one form of the irradiation apparatus of the present invention is there illustrated and generally designated by the numeral 12. The apparatus of this form of the invention comprises a housing 14 having interconnected top, bottom and sidewalls 16, 18, and 20 respectively that define an internal chamber 22. Carried by top wall 16 is filter means filter for blocking white light from the UV sources 24 that are disposed within internal chamber 22. The filter means here comprises a UV transmitting light blocking filter 26. Filter 26 is adapted to carry an article, such as a specimen that is to be irradiated as, for example, a ploynucleocide. In the present form of the invention, filter 26 blocks white light.

Figure 2:
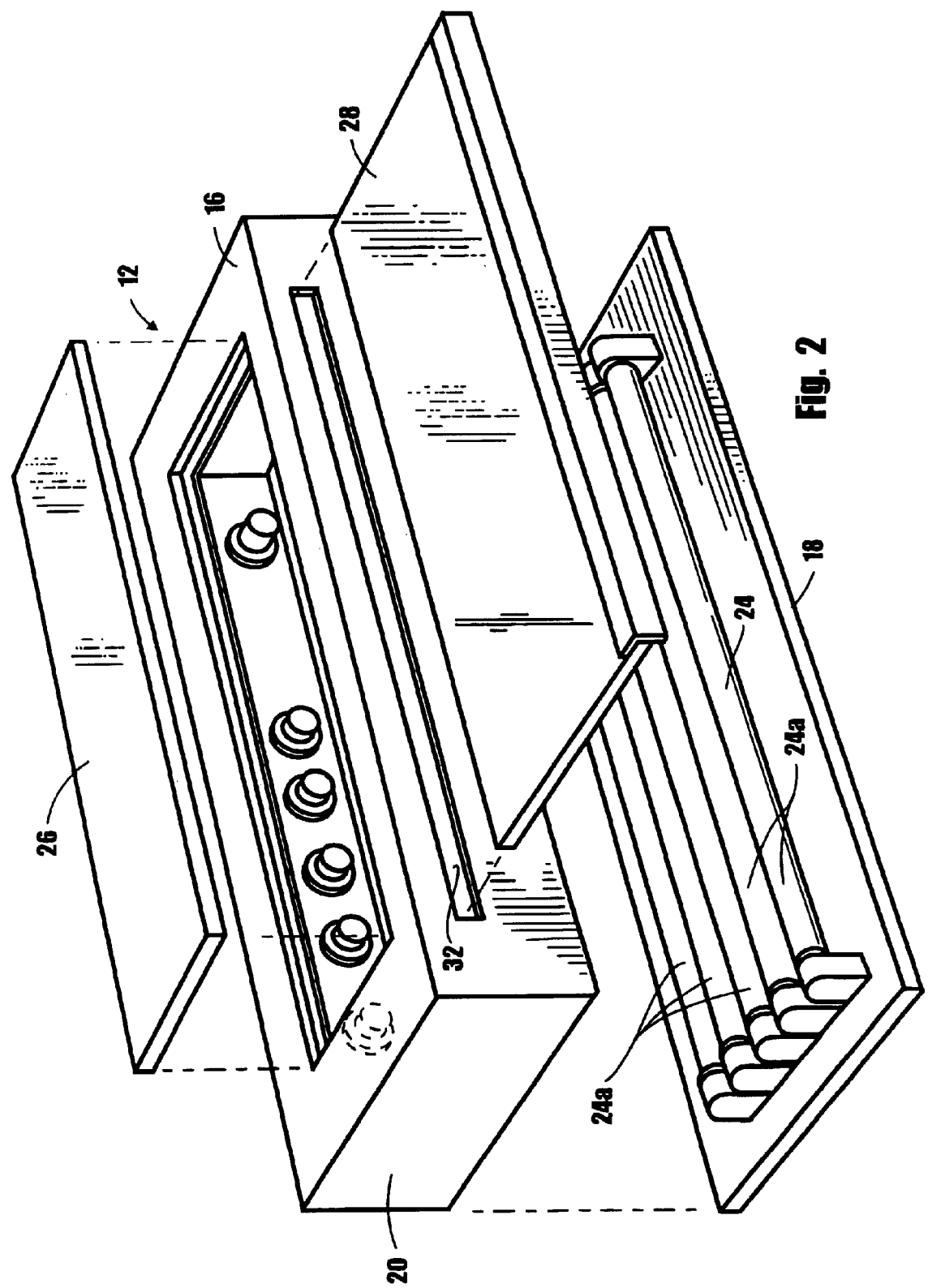
FIG. 2 is a generally perspective, exploded view of the apparatus shown in FIG. 1.
Figure 3:
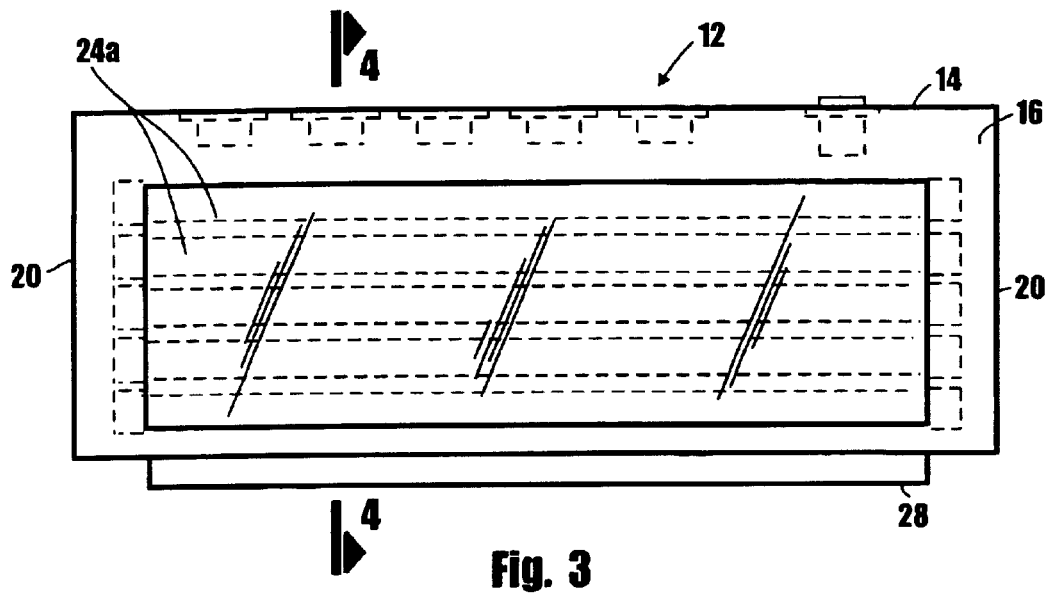
FIG. 3 is a top plan view of the apparatus shown in FIG. 1.
Figure 5:
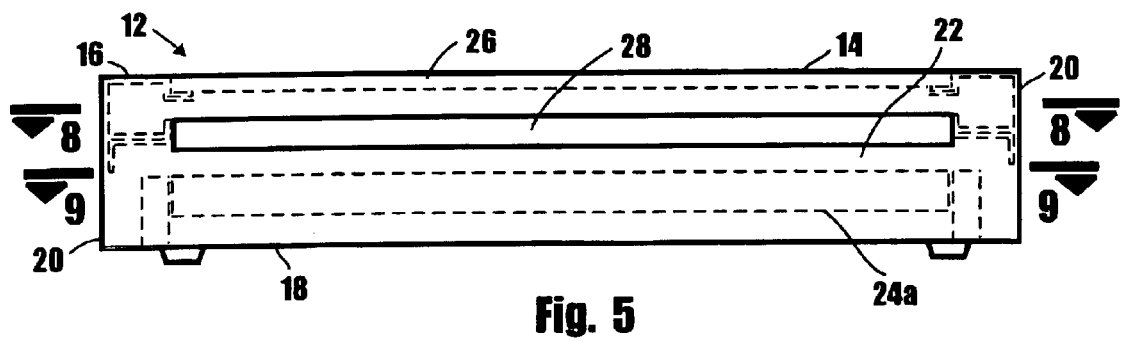
FIG. 5 is a side elevational view of the apparatus shown in FIG. 1.
Figure 6:
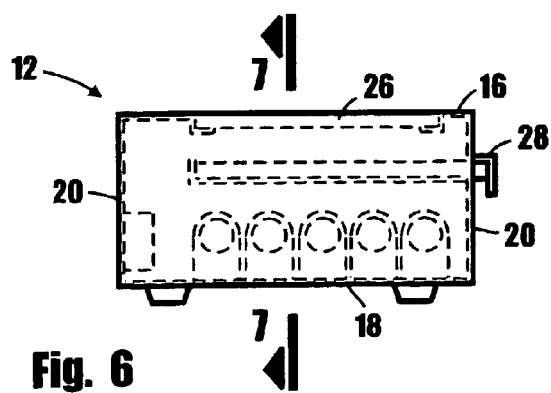
FIG. 6 is an end view of the apparatus shown in FIG. 1.
Figure 7:
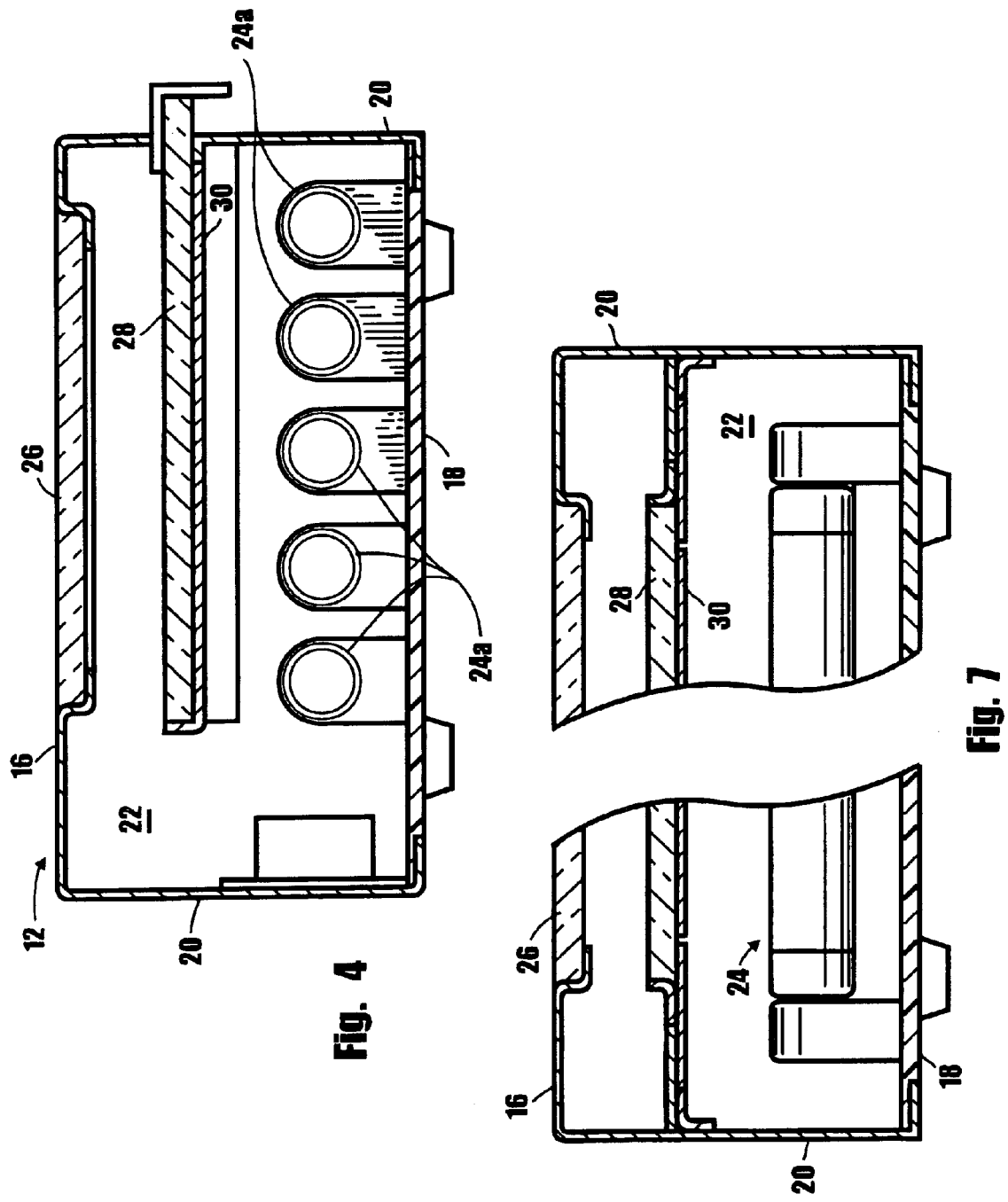
FIG. 7 is a cross-sectional view taken along lines 7—7 of FIG. 6.
Figure 8:
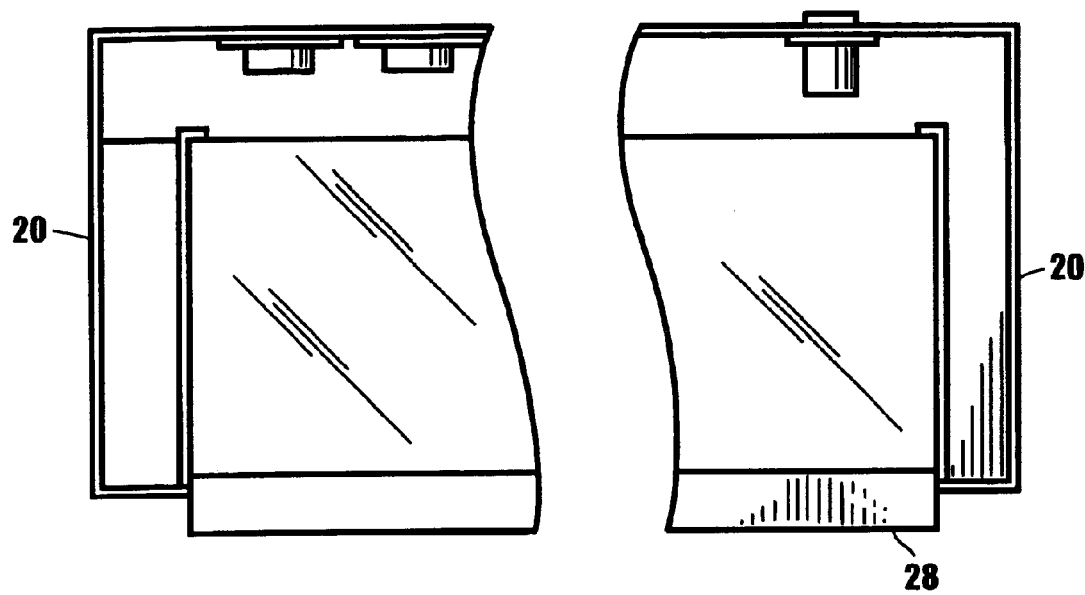
FIG. 8 is a cross-sectional view taken along lines 8—8 of FIG. 5.
Figure 9:
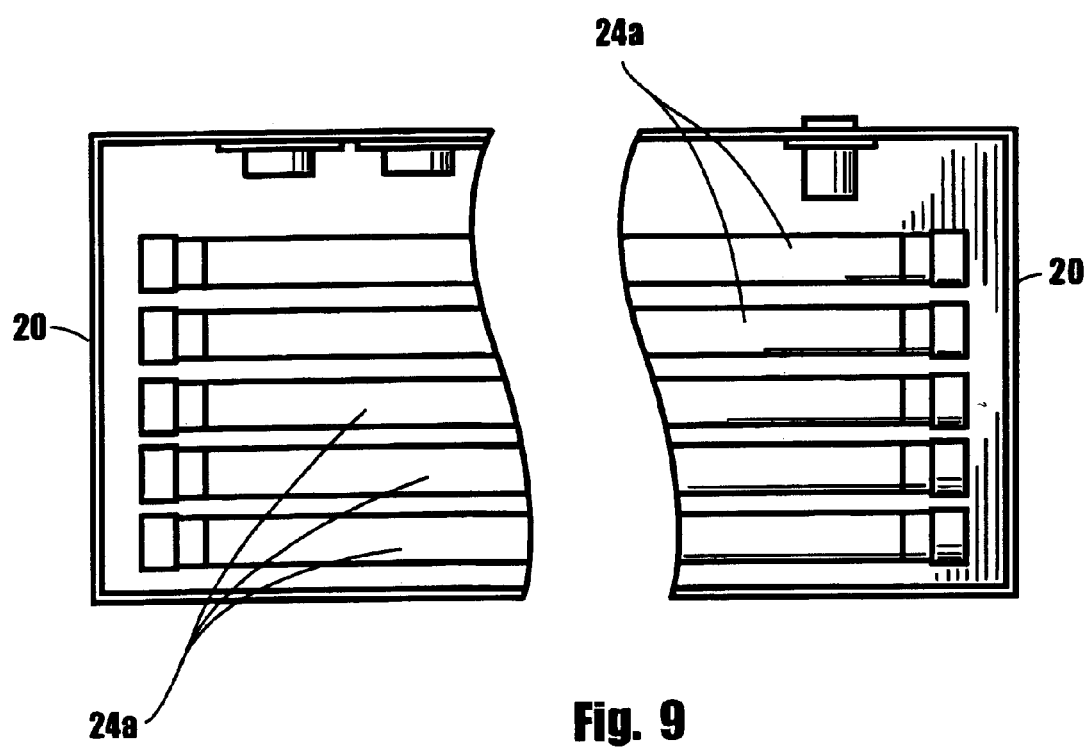
FIG. 9 is a cross-sectional view taken along lines 9—9 in FIG. 5.
Figure 10:
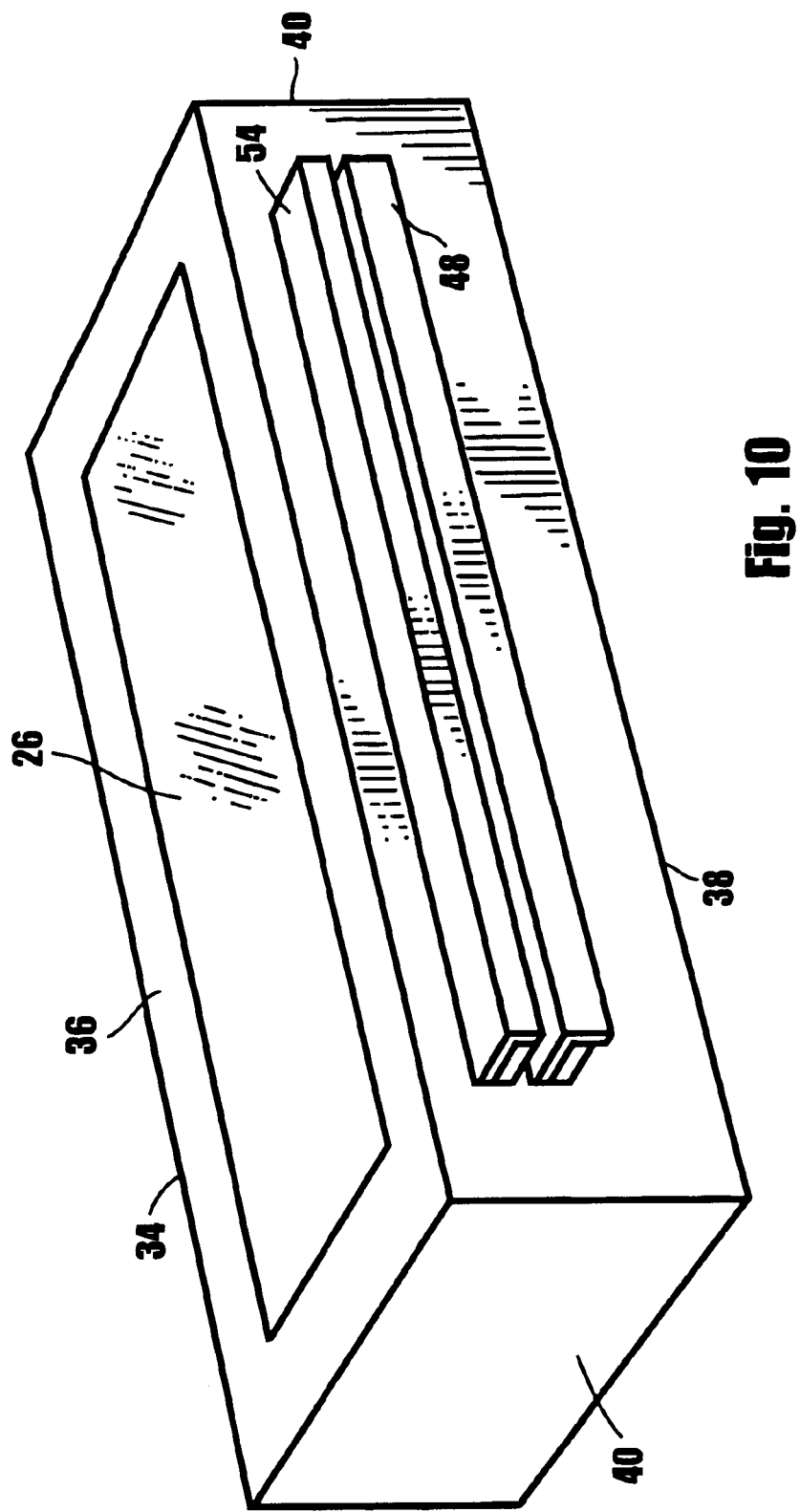
FIG. 10 is a generally perspective view of an alternate form of the apparatus of the invention.
Figure 13:
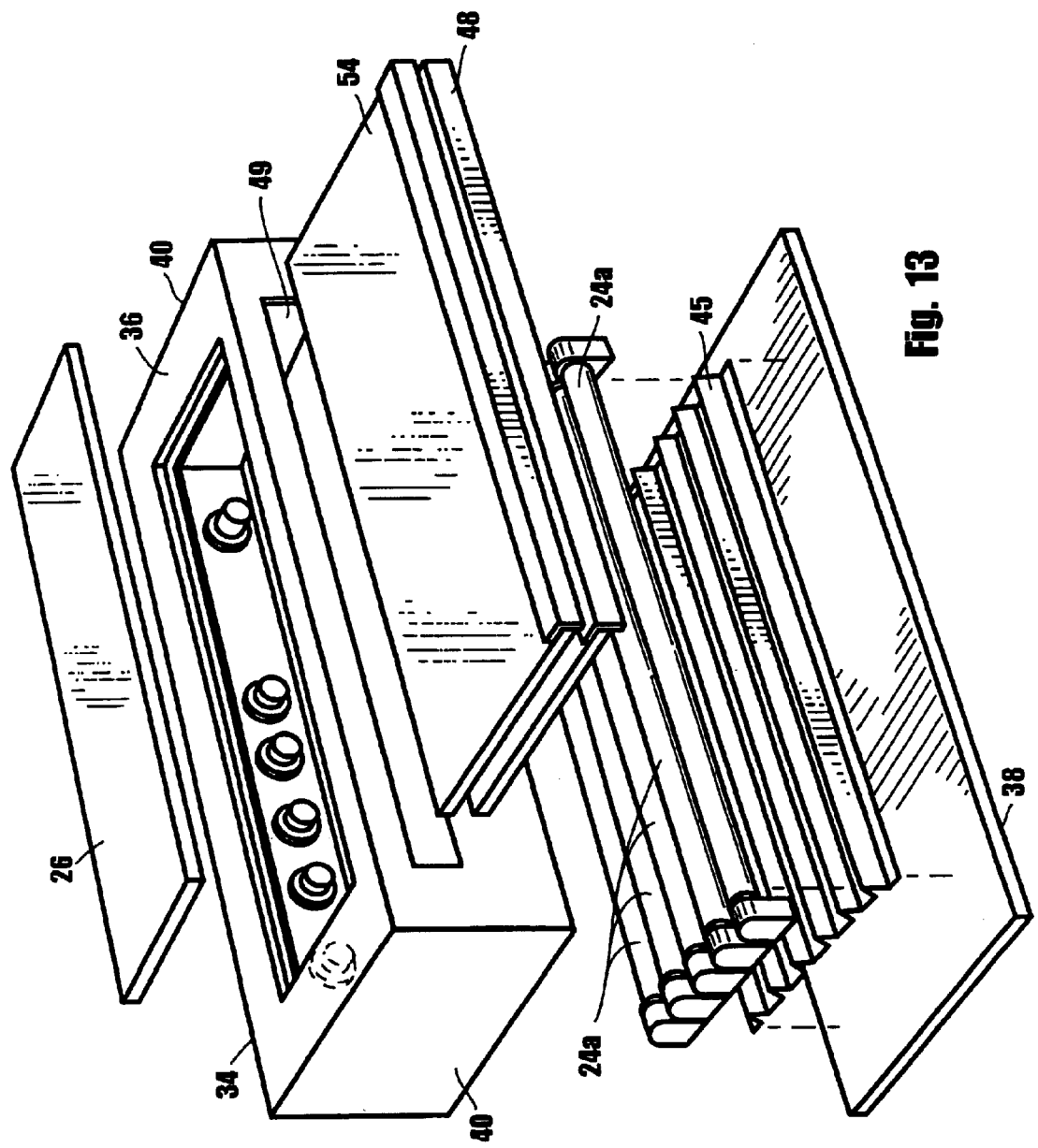
FIG. 13 is a generally perspective, exploded view of the alternate form of the apparatus shown in FIG. 10.

As best seen in FIG. 2, the UV sources here comprises a plurality of spaced-apart, ultraviolet-light-emitting lamps 24a that emit UV radiation at a first wavelength of, for example, 254 nanometers. Positioned between the array of lamps 24a and filter 26 is the highly novel first wavelength conversion means of the invention which is adapted to convert the UV radiation at the first wavelength to UV radiation at a second wavelength of, for example, about 365 nanometers or about 312 nm. This first wavelength conversion means here comprises a conversion plate 28 that is removably carried by housing 14 at a location intermediate filter 26 and UV source 24. More particularly, plate 28 is provided with a wave shifting phosphor coating 30 (FIGS. 4 and 7) and is slidably movable within a slot 32 formed in housing. With this construction, plate 28 can be readily removed from the housing and replaced with another plate if desired. As is well known in the art, phosphors are compounds that are capable of emitting useful quantities of radiation in the visible and/or ultraviolet spectrums upon excitation of the material by an external energy source. Due to this property, phosphor compounds have long been utilized in cathode ray tube (CRT) screens for televisions and similar devices. Typically, inorganic phosphor compounds include a host material doped with a small amount of an activator ion. In recent years, phosphor compounds, including phosphors in particulate form, have been used in display devices, decorations, cathode ray tubes, and fluorescent lighting fixtures. Luminescence or light emission by phosphor particles may be stimulated by application of heat (thermoluminescence), light (photoluminescence), high energy radiation (e.g., x-rays or e-beams), or electric fields (electroluminescence). A comprehensive discussion of various types of phosphors can be found in U.S. Pat. No. 6,193,908 issued to Hampden-Smith et al.

Turning to FIGS. 10 through 13, an alternate form of transilluminator of the invention is there shown. This form of the invention is similar in many respects to that shown in FIGS. 1 through 9 and like numerals are used in FIGS. 10 through 13 to identify like components. This alternate form of the invention comprises a housing 34 having interconnected top, bottom and sidewalls 36, 38, and 40 respectively that define an internal chamber 42. Carried by top wall 36 is filter means filter for blocking white light from the UV sources 24 that are disposed within internal chamber 42. The filter means here comprises a UV transmitting white light blocking filter 26. As before, filter 26 is adapted to carry an article, such as a specimen that is to be irradiated.

As best seen in FIG. 11, the UV sources here comprises a plurality of spaced-apart, ultraviolet-light-emitting lamps 24a that emit UV radiation at a first wavelength of, for example, 254 nanometers. Lamps 24a are here positioned over a corrugated reflector 45. For certain application, reflector 45 can also be flat or dimpled. Positioned between the array of lamps 24a and filter 26 are first and second wavelength conversion means which are adapted to convert the UV radiation at the first wavelength to UV radiation at a second wavelength of, for example, about 312 nanometers and then to UV radiation at a third wavelength of, for example, about 365 nanometers. This first wavelength conversion means here comprises a first conversion plate 48 that is removably carried by housing 34 within a slot 49 at a location intermediate filter 26 and UV source 24. In this instance, plate 48 is provided with a wave shifting phosphor coating 50 (FIGS. 11 and 12) and is slidably movable within the slot 49 that is formed in housing. The second wavelength conversion means of this latest form of the invention comprises a second conversion plate 54 that is also removably carried by housing 34 within slot 49. Plate 54 is provided with a wave shifting phosphor coating 56 (FIGS. 11 and 12) and is slidably movable within the slot 49. Plate 54 is disposed at a location intermediate plate 48 and filter 26 in the manner shown in the drawings. With the construction shown, either or both plates 48 and 54 can be readily removed from the housing and replaced with alternate plates if desired.

Figure 14:
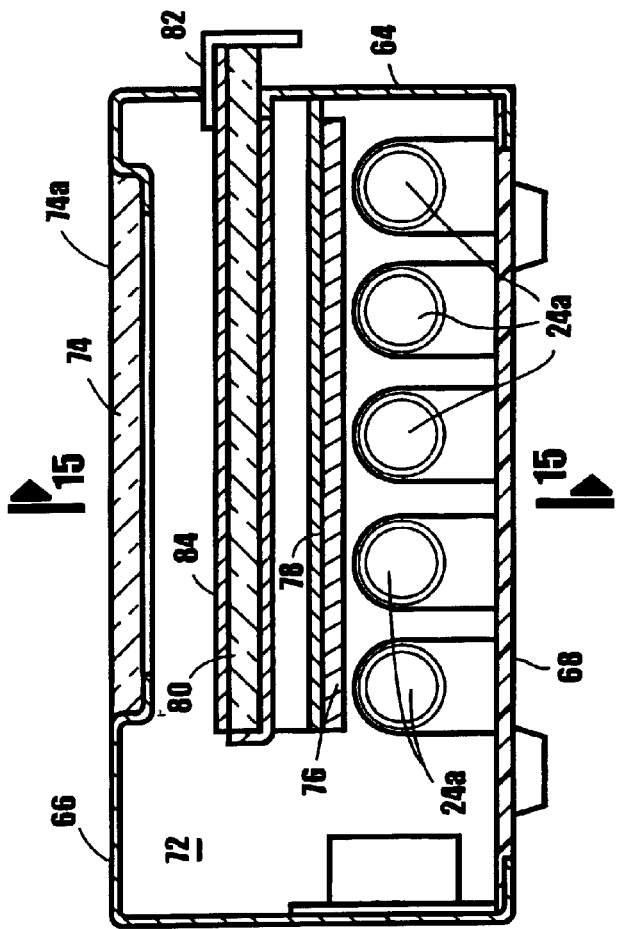
FIG. 14 is a transverse cross-sectional view of another form of the apparatus of the invention.
Figure 15:
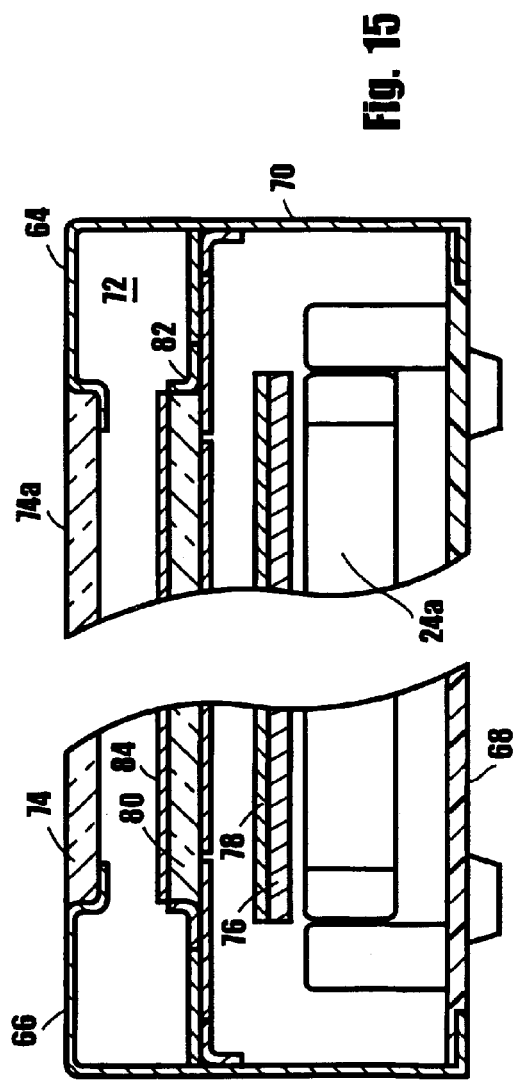
FIG. 15 is a cross-sectional view taken along lines 15—15 of FIG. 14.

Referring now to FIGS. 14 and 15, another form of transilluminator of the invention is there shown for controllably irradiating with ultraviolet radiation for use in controllably irradiating an object with ultraviolet radiation. This form of the invention, which separates the UV producing components from the sample to be exposed, is similar in many respects to that shown in FIGS. 10 through 13 and like numerals are used in FIGS. 14 and 15 to identify like components. This alternate form of the invention comprises a housing 64 having interconnected top, bottom and sidewalls 66, 68, and 70 respectively that define an internal chamber 72. Carried by top wall 66 is a UV transmitting, light blocking element 74 here provided in the form of a borosilicate glass. Element 74 includes a generally planar upper surface 74a that is adapted to carry an article, such as a specimen that is to be irradiated.

Borosilicate glass, or light blocking element 74, functions to create a platform that minimizes the transmission of 254 nm ultraviolet radiation, while effectively transmitting a midrange 312 nm ultraviolet and above. It is to be understood that blocking element 74 can be constructed of a quartz material, fused silica, a hard glass, such as chemical Pyrex, lime glass, sapphire glass or ultraviolet transmitting or minimizing Plexiglass.

As illustrated in the drawings, the UV sources here comprises a plurality of spaced-apart, ultraviolet-light-emitting lamps 24a that emit UV radiation at a first wavelength of, for example, 254 nanometers. Positioned between the array of lamps 24a and element 74 are first and second wavelength conversion means which are adapted to convert the UV radiation at the first wavelength to UV radiation at a second wavelength of, for example, about 312 nanometers and then to UV radiation at a third wavelength of, for example, about 365 nanometers. This first wavelength conversion means here comprises a first or midrange phosphor plate 76 that is fixedly mounted within housing 64. Phosphor plate 76 here comprises a borosilicate, or like glass that is coated with a phosphor coating that converts 254 nm ultraviolet (short wave ultraviolet) to about 312 nm ultraviolet (midrange ultraviolet).

Superimposed over plate 76 is a short wave UV filter 78 which blocks ambient white visible light, while transmitting 254 nm, 312 nm and 365 nm ultraviolet radiation.

The second wavelength conversion means of this latest form of the invention comprises a second or long wave UV phosphor plate 80 that is removably carried by housing 64 within a slot 82. Plate 80, which is coated with a phosphor, can be constructed from borosilicate glass, quartz glass, hard glass, lime glass, or Plexiglas that only transmits 365 nm ultraviolet radiation. Superimposed over plate 80 is a long wave UV transmitting filter 84 that transmits only 365 nm ultraviolet radiation and effectively blocks ambient white, visible light transmission. As illustrated in the drawings, plate 80 and filter 84 are disposed at a location intermediate plate 76 and element 74. With the construction shown in the drawings, if desired plate 80 can be readily removed from the housing and replaced with a plate of alternate construction.

Turning next to FIGS. 16 and 17, still another form of transilluminator of the invention for irradiation is there shown for use in controllably irradiating an object with ultraviolet radiation. This form of the invention is also similar in many respects to that shown in FIGS. 10 through 13 and like numerals are used in FIGS. 16 and 17 to identify like components. This alternate form of the invention, which comprises an apparatus for changing a UV source to a multiple UV wavelength source with or without a UV transmitting, ambient white blocking filter, includes a housing 88 having interconnected top, bottom and sidewalls 90, 92, and 94 respectively that define an internal chamber 96. Carried by top wall 90 is a UV transmitting, light blocking element 74 here provided in the form of a borosilicate glass. Element 74 includes a planar upper surface 74a that is adapted to removably carry an assemblage 98 made up of a glass or other appropriate material plate 100 having first and second surfaces 100a and 100b and phosphor coating 102, which is affixed to surface 100b, is designed to convert ultraviolet radiation at a first wavelength to ultraviolet radiation at a second wavelength. Upper surface 100a of plate 100 is substantially planar and is adapted to support a specimen that is to be irradiated. In the performance of certain operations assemblage 98 can be readily removed from the apparatus and, if desired, can be replaced by an assembly having different characteristics.

As in the previously described embodiments of the invention, the UV sources here comprises a plurality of spaced-apart, ultraviolet-light-emitting lamps 24a that emit UV radiation at a first wavelength of, for example, 254 nanometers.

Positioned between the array of lamps 24a and element 74 is fixedly mounted plate 104 that is coated with a phosphor coating 106 that is designed to convert UV radiation at a first wavelength to UV radiation at a second wavelength. Fixedly mounted between plate 104 and plate 74 is a filter 108 that is the character well understood by those skilled in the art and functions to filter out certain UV wavelengths.

Figure 16A:
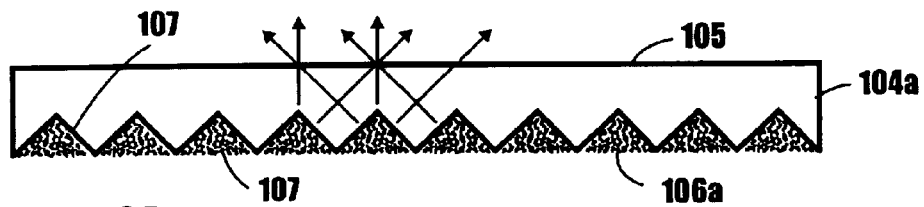
FIG. 16A is a side-elevational view of an alternate form of conversion plate of the invention.

Referring to FIG. 16A there is shown an alternate form of conversion plate 104a that is coated with a phosphor coating 106a. Plate 104a, which can be constructed from borosilicate, quartz, plastic or like materials, has a generally planar upper surface 105 and a grooved surface 107 which carriers the phosphor coating 106a. The novel step of grooving surface 107 substantially increases the surface area to which the phosphor can adhere. Additionally, as indicated by the arrows of FIG. 16A, the UV radiation emitted from the UV sources 24a is uniquely scattered as it impinges on the irregular, grooved surface, thereby increasing the diffusion of the light as it is converted to a selected wavelength by the converting phosphor. The uniformly grooved surface 107 not only increases the dispersion of the light, but also enhances the uniformity thereof.

Figure 16B:
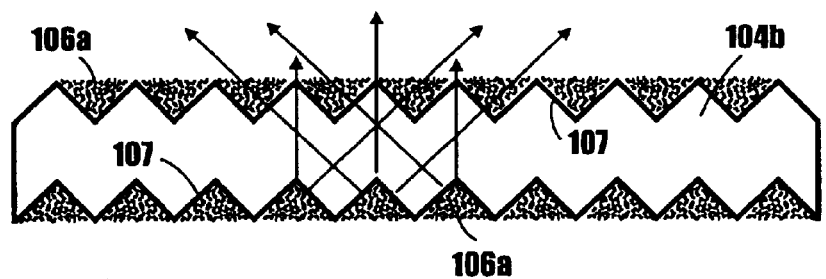
FIG. 16B is a side-elevational view of still another form of conversion plate of the invention.

Turning next to FIG. 16B, still another form of conversion plate 104b that is coated with a phosphor coating 106a, is there shown. Plate 104b, which can be constructed from borosilicate, quartz, plastic or like materials, has opposed grooved surfaces 107, both of which carry the phosphor coating 106a. As indicated by the arrows of FIG. 16B, the UV radiation emitted from the UV sources 24a is uniquely deflected by the angled walls of the grooved surfaces 107 as it is converted to a selected wavelength by the converting phosphor.

Figure 16C:
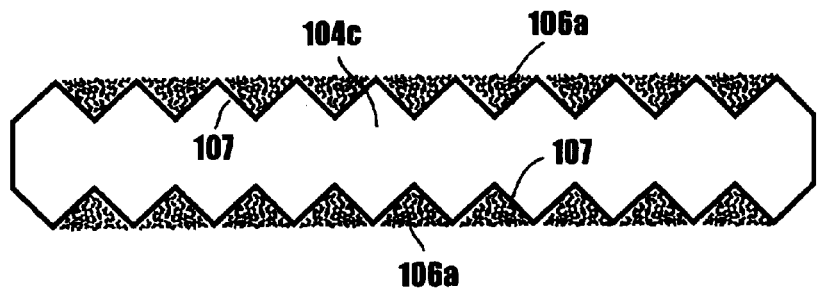
FIG. 16C is a side-elevational view of yet another form of conversion plate of the invention.

FIG. 16C shows yet another form of conversion plate 104c that is coated with a phosphor coating 106a. Plate 104c, which can be constructed from borosilicate, quartz, plastic or like materials, is of a similar configuration to conversion plate 104b save for the fact that the grooved surfaces are offset rather than being aligned as shown in FIG. 16B. As in the previously described embodiment of the invention both of the grooved surfaces are controllably coated by a selected conversion phosphor.

Figure 16D:
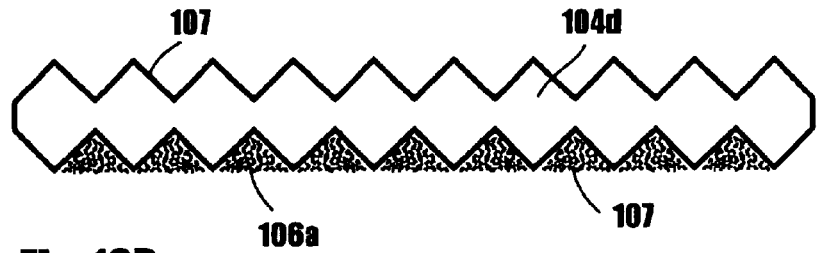
FIG. 16D is a side-elevational view of still another form of conversion plate of the invention.

Referring to FIG. 16D still another form of conversion plate 104d that is coated with a phosphor coating 106a. Plate 104d is identical in construction to plate 104b, but only one surface of the plate is coated with a phosphor coating 106a.

It is to be understood that, while the drawing show that the phosphor coating fills the grooves in the plates, for certain applications only the surface of the grooves are evenly and more lightly coated with the selected phosphor.

As previously mentioned, the advantages of the plate configuration shown in FIGS. 16A, 16B, 16C and 16D include the provision of greater surface areas for the phosphor to adhere to and greater scattering or diffusion of the radiation to thereby enhance the uniformity of emission.

As in the previously described embodiments, the UV sources here comprises a plurality of spaced-apart, ultraviolet-light-emitting lamps 24a that emit UV radiation at a first wavelength of, for example, 254 nanometers.

Positioned between the array of lamps 24a and element 74 is fixedly mounted plate 104 that is strategically coated with a phosphor coating 106. Fixedly mounted between plate 104 and plate 74 is the previously identified filter 108.

Figure 18:
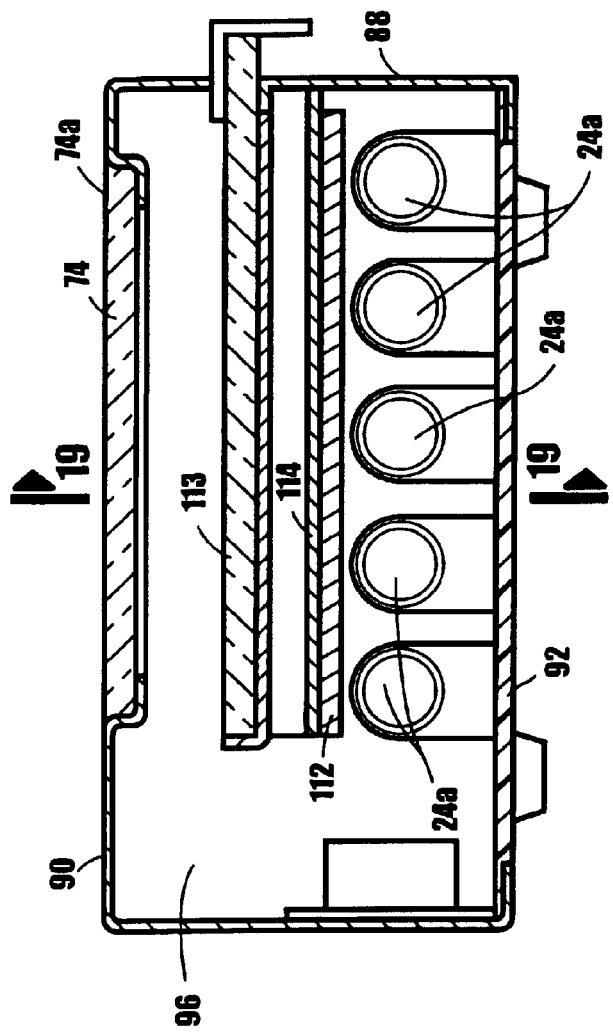
FIG. 18 is a transverse cross-sectional view of another form of the apparatus of the invention.
Figure 19:
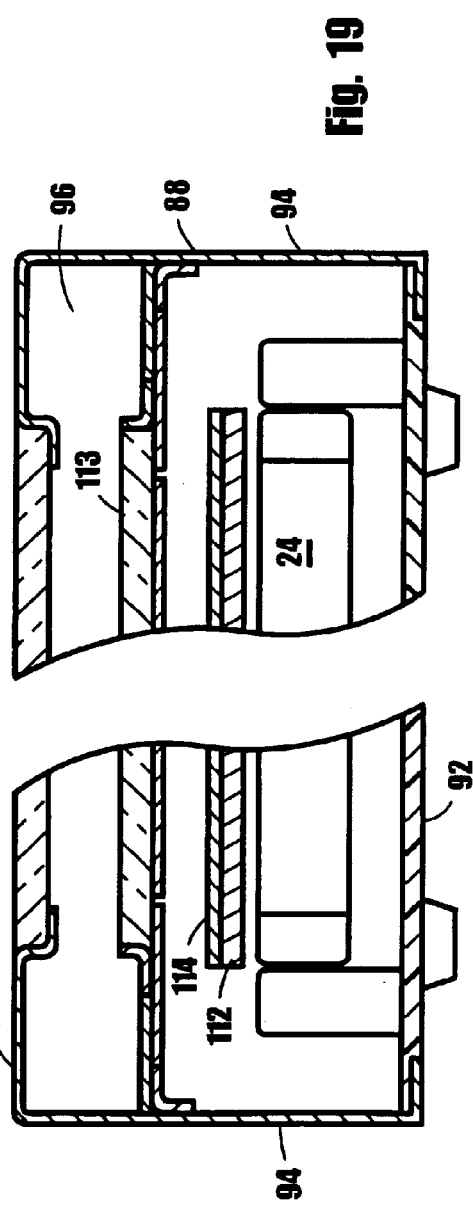
FIG. 19 is a cross-sectional view taken along lines 19—19 of FIG. 18.

Referring to FIGS. 18 and 19 yet, another form of transilluminator of the invention is there shown. This form of the invention which permits the selective exposure of a sample with broadband UV of about 312 nm and about 365 nm in a simple, cost effective manner, is similar in many respects to that shown in FIGS. 14 through 17 and like numerals are used in FIGS. 18 and 19 to identify like components. This latest form of the invention comprises a housing 88 having interconnected top, bottom and sidewalls 90, 92, and 94 respectively that define an internal chamber 96. Carried by top wall 90 is a UV transmitting, light blocking element 74 here provided in the form of a borosilicate glass. Element 74 includes a planar upper surface 74a that is adapted to removably carry an assemblage 98 made up of a glass plate 100 having first and second surfaces 100a and 100b and a phosphor coating 102 affixed to surface 100b that is designed to convert ultraviolet radiation at a first wavelength to ultraviolet radiation at a second wavelength. Upper surface 100a is substantially planar and adapted to support a specimen that is to be irradiated. In the performance of certain operations assemblage 98 can be readily removed from the apparatus and, if desired, can be replaced by an assembly having different characteristics. This latest form of the invention, element 74 includes a planar upper surface 74a that is adapted to carry an article, such as a specimen that is to be irradiated. Element 74 can be constructed of a suitable glass or Plexiglas material that transmits only 365 nm bandwidth radiation.

As in the previously described embodiments, the UV sources here comprises a plurality of spaced-apart, ultraviolet-light-emitting lamps 24a that emit UV radiation at a first wavelength of, for example, 254 nanometers.

Positioned between the array of lamps 24a and element 74 is a fixedly mounted plate 112 that is coated with a mixture of phosphor coatings 114 which converts 254 nm radiation (short wave UV) to a broadband ultraviolet radiation of between approximately 312 nm and approximately 365 nm. Removably mounted between plate 112 and plate 74 is a filter 113 for blocking passage of all but UV radiation at approximately the 365 nm bandwidth. It is to be noted that because of the unique, removable filter 113 which is embodied in this latest form of the apparatus of the invention, two wavelengths of ultraviolet are permitted, namely a wavelength of approximately 365 nm and a wavelength of approximately 312 nm. More particularly, when filter 113 is in position between plates 74 and 112, the transmission of ultraviolet radiation is restricted to only the 365 nm bandwidth. Conversely, when filter 112 is retracted from the housing, transmission of ultraviolet radiation at wavelengths of both in 365 nm and 312 nm is permitted.

Figure 20:
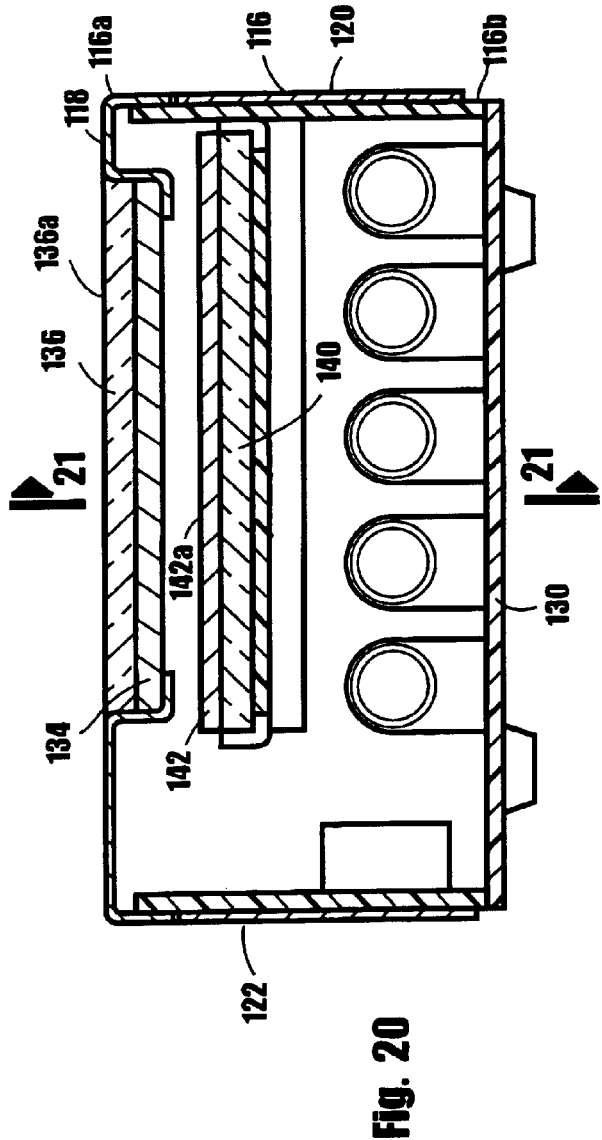
FIG. 20 is a transverse cross-sectional view of yet another form of transilluminator apparatus of the invention.
Figure 21:
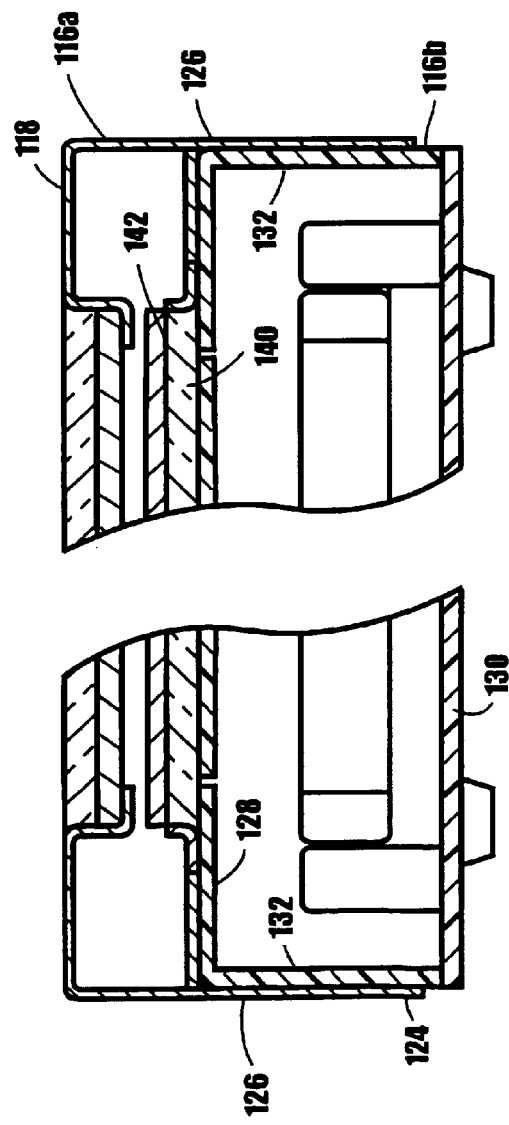
FIG. 21 is a cross-sectional view taken along lines 21—21 of FIG. 20.

Turning next to FIGS. 20 and 21, still another form of transilluminator of the invention for controllably irradiating an object with ultraviolet radiation is there shown. This form of the invention, which enables the user to change UV wavelengths without having to use a multiplicity of UV lamps emitting radiation of differing wavelengths, is also similar in some respects to that shown in FIGS. 10 through 13 and like numerals are used in FIGS. 20 and 21 to identify like components. This alternate form of the invention comprises a housing 116 having a top portion 116a and a bottom portion 116b. Top portion 116a, which is slidably receivable over bottom portion 116b includes interconnected top, front, back, bottom and sidewalls 118, 120, 122, 124 and 126 respectively. Bottom portion 116b includes top, bottom and sidewalls 128, 130 and 132 respectively. Carried by top wall 118 is a UV transmitting, light blocking element 134 here provided in the form of a borosilicate glass. Superimposed on element 134 is an ultraviolet transmitting filter 136 that only transmits a bandwidth of 365 nm ultraviolet radiation while blocking ambient white light transmission. Filter 136 includes a generally planar top surface 136a that is adapted to support an article, such as the specimen that is to be irradiated.

Borosilicate glass, or light blocking element 134, like the previously identified element 74, functions to create a platform that minimizes the transmission of 254 nm ultraviolet radiation, while effectively transmitting a midrange 312 nm ultraviolet radiation and above. It is to be understood that blocking element 134 can be constructed of a quartz material, a hard glass, such as chemical Pyrex, limeglass, or ultraviolet transmitting Plexiglass. Long wave UV transmitting filter 136 transmits only 365 nm ultraviolet radiation and effectively blocks ambient white light transmission.

As in the earlier described embodiments of the invention, and as illustrated in the drawings, the UV sources here comprise a plurality of spaced-apart, ultraviolet-light-emitting lamps 24a that emit UV radiation at a first wavelength of, for example, 254 nanometers.

Positioned between the array of lamps 24a and element 134 is a midrange phosphor plate 140 that is fixedly mounted within housing portion 116b. The phosphor plate 140 here comprises a borosilicate, or like glass that is coated with a phosphor coating that converts 254 nm ultraviolet (short wave ultraviolet) to 312 nm ultraviolet (midrange ultraviolet).

Mounted on plate 140 is a short wave UV filter 142 which blocks ambient white light, while transmitting 254 nm, 312 nm and 365 nm ultraviolet radiation.

With the construction shown in FIGS. 20 and 21, the upper portion of 116a of the housing can be readily separated from the lower portion 116b so as to expose the upper surface 142a of filter 142. With the upper portion 116a of the housing removed, the specimen to be irradiated can be placed directly on the upper surface 142a of the filter.

Turning next to FIGS. 22 and 23, still another form of transilluminator of the invention is there shown. This form of the invention uniquely embodies a novel fibrous or mesh assembly that has been coated or impregnated with selected wavelength conversion phosphors. This latest form of the invention is similar in many respects to that shown in FIGS. 18 and 19 and, once again, like numerals are used in FIGS. 22 and 23 to identify like components. This latest form of the invention comprises a housing 148 having interconnected top, bottom and sidewalls 150,152 and 154 respectively that define an internal chamber 156. Carried by top wall 150 is a UV transmitting, light blocking element 74 here provided in the form of a borosilicate glass. As before, element 74 includes a planar upper surface 74a that is adapted to carry an article, such as a specimen that is to be irradiated. Element 74 can be constructed of a suitable glass or Plexiglas material that transmits only 365 nm bandwidth radiation.

As in the previously described embodiments, the UV sources here comprise a plurality of spaced-apart, ultraviolet-light-emitting lamps 24a that emit UV radiation at a first wavelength of, for example, 254 nanometers.

Figure 24:
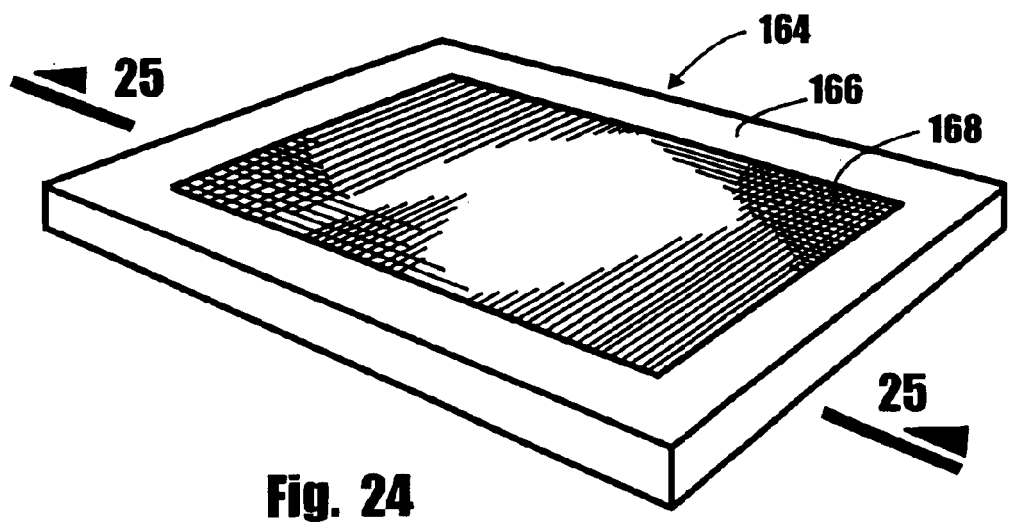
FIG. 24 is a generally perspective view of one form of a coated screen component that is usable in the apparatus of the invention for irradiating an object with ultraviolet radiation.
Figure 25:
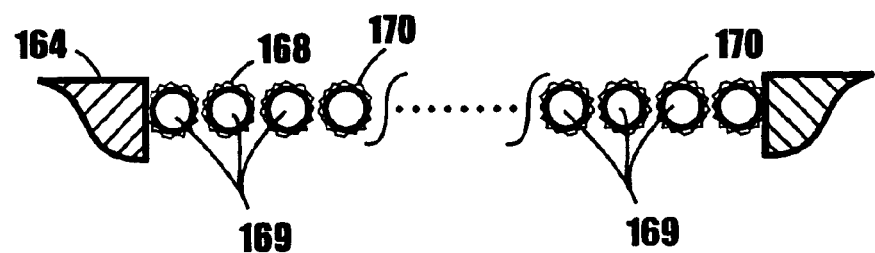
FIG. 25 is a cross-sectional view taken along lines 25—25 of FIG. 24.

Positioned between the array of lamps 24a and element 74 is a removably mounted filter 160. Mounted between filter 160 and lamps 24a is a borosilicate glass plate 162 and a conversion means for converting ultraviolet radiation at a first wavelength to ultraviolet radiation at a second wavelength. This conversion means here uniquely comprises a novel phosphor coated mesh assembly 164 which is of general character illustrated in FIGS. 24 and 25. As best seen in FIG. 24, mesh assembly 164 includes supporting means here provided as a supporting frame 166 that functions to support a mesh substrate 168 in a stretched, generally planar configuration. Mesh substrate 168 comprises a multiplicity of spaced apart, interconnected elements 169, each of which is at least partially coated with a phosphor so as to create a large area, uniform lighting background. Mesh substrate 168 can be formed from metal, plastic, glass, quartz and like materials. The mesh substrate can be coated with various wave shift phosphors 170, such as phosphors that will convert 254 nm ultraviolet radiation to 312 nm ultraviolet radiation; will convert 254 nm ultraviolet radiation to 365 nm ultraviolet radiation; will convert 354 nm ultraviolet radiation to 302 nm/365 nm radiation (broadband mix); and will convert 254 nm ultraviolet radiation to a UV, white light combination. Wave-shift phosphors 170 can also comprise a mixture of visible conversion spectra phosphors and ultraviolet phosphors.

As in certain of the of the earlier described embodiments of the invention, light sources 24a are positioned over a corrugated reflector 172 (FIG. 22) which functions to uniformly reflect the light omitted from the light sources upwardly into internal chamber 156. As before, reflector 172 can be a flat reflector or a dimpled plate reflector.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:
1. An apparatus for irradiating an object with ultraviolet radiation comprising:
    (a) a housing having a top wall and an internal chamber;
    (b) a source of ultraviolet radiation disposed within said chamber for emitting ultraviolet light at a first wavelength;
    (c) an ultraviolet radiation transmitting, light blocking element carried by said top wall of said housing;
    (d) a first phosphor plate fixedly mounted within said housing between said source of ultraviolet radiation and said ultraviolet radiation transmitting, light blocking element for converting short wave ultraviolet radiation to midrange ultraviolet radiation;
    (e) a short wave ultraviolet filter superimposed over said first phosphor plate for transmitting short wave ultraviolet radiation and for blocking ambient white light;
    (f) a second phosphor plate removably carried by said housing between said short wave ultraviolet filter and said ultraviolet radiation transmitting, light blocking element for blocking ambient white light; and
    (g) a long wave ultraviolet filter superimposed over said second phosphor plate for transmitting long wave ultraviolet radiation.

2. The apparatus as defined in claim 1 in which said source of ultraviolet radiation emits radiation at a wave length of about 254 nanometers and in which said ultraviolet radiation transmitting, light blocking element transmits radiation at a wavelength of at least approximately 312 nanometers.

3. The apparatus as defined in claim 1 in which said source of ultraviolet radiation emits radiation at a wavelength of about 254 nanometers and in which said first phosphor plate converts the 254 nanometers radiation to approximately 312 nanometers radiation.

4. The apparatus as defined in claim 1 in which said short wave ultraviolet filter transmits ultraviolet radiation at wavelengths of about 254, 312 and 365 nanometers.

5. The apparatus as defined in claim 1 in which said long wave ultraviolet filter transmits ultraviolet radiation at a wavelength of only about 365 nanometers.

6. The apparatus as defined in claim 1 in which said glass plate has first and second surfaces and in which said coating is affixed to said second surface.

7. The apparatus as defined in claim 1 in which said long wave ultraviolet filter transmits ultraviolet radiation at a wavelength of only about 365 nanometers.

8. The apparatus as defined in claim 7 in which said phosphor plate converts ultraviolet radiation at a wavelength of about 254 nanometers to ultraviolet radiation at a wavelength of about 312 nanometers.

9. The apparatus as defined in claim 7 in which said ultraviolet radiation transmitting, light blocking element comprises borosilicate glass.

10. The apparatus as defined in claim 7 in which said phosphor plate includes at least one grooved surface.

11. An apparatus for irradiating an object with ultraviolet radiation comprising:
    (a) a housing having a top wall and an internal chamber;
    (b) a source of ultraviolet radiation disposed within said chamber for emitting ultraviolet light at a first wavelength;
    (c) an ultraviolet radiation transmitting, light blocking element carried by said top wall of said housing;

(d) an assemblage removably mounted upon said ultraviolet radiation transmitting, light blocking element for converting ultraviolet radiation at a first wavelength to ultraviolet radiation at a second wavelength;

(e) a phosphor plate fixedly mounted within said housing between said assemblage and said ultraviolet radiation transmitting, light block element for converting ultraviolet radiation at a first wavelength to ultraviolet radiation at a second wavelength; and (f) a filter disposed between said phosphor plate and said ultraviolet radiation transmitting, light blocking element for filtering selected wavelengths of ultraviolet radiation.

12. The apparatus as defined in claim 11 in which said assemblage comprises a glass plate and a phosphor coating affixed to said glass plate for converting ultraviolet radiation at a first wavelength to ultraviolet radiation at a second wavelength.

13. An apparatus for irradiating an object with ultraviolet radiation comprising:

(a) a housing having a top wall and an internal chamber;

(b) a source of ultraviolet radiation disposed within said chamber for emitting ultraviolet light at a first wavelength;

(c) an ultraviolet radiation transmitting, light blocking element carried by said top wall of said housing;

(d) a plate fixedly mounted within said housing between said source of ultraviolet radiation and said ultraviolet radiation transmitting, light blocking element, said plate having a coating comprising a mixture of phosphors for converting short wave ultraviolet radiation to broadband ultraviolet radiation; and (e) a filter removably mounted within said housing between said plate and said ultraviolet radiation transmitting, light blocking element for blocking passage of all but ultraviolet radiation at a wavelength of about 365 nanometers.

14. An apparatus as defined in claim 13 in which said source of ultraviolet radiation emits radiation at a wavelength of about 254 nanometers and in which said mixture of phosphors converts 254 nanometers radiation to ultraviolet radiation at a wavelength of between about 312 nanometers radiation and about 365 nanometers radiation.

15. An apparatus for irradiating an object with ultraviolet radiation comprising:

(a) a housing having a top portion and a bottom portion, said top portion being removably connected to said bottom portion, said housing having an internal chamber;

(b) a source of ultraviolet radiation disposed within said internal chamber for emitting white light and ultraviolet light at a first wavelength;

(c) an ultraviolet radiation transmitting, light blocking element carried by said top portion of said housing;

(d) an ultraviolet filter superimposed over said ultraviolet radiation transmitting, light blocking element for transmitting ultraviolet radiation at a wavelength of only about 365 nanometers;

(e) a phosphor plate fixedly mounted within said housing between said source of ultraviolet radiation and said ultraviolet radiation transmitting, light blocking element for converting short wave ultraviolet radiation to midrange ultraviolet radiation; and (f) filter means superimposed over said phosphor plate for filtering white light from the radiation emitted from said source of ultraviolet radiation and for transmitting ultraviolet radiation at wavelengths of about 245, 312 and 365 nanometers.

16. An apparatus for irradiating an object with ultraviolet radiation comprising:

(a) a housing having a top wall and an internal chamber;

(b) a source of ultraviolet radiation disposed within said chamber for emitting ultraviolet light at a first wavelength;

(c) an ultraviolet radiation transmitting, light blocking element carried by said top wall of said housing;

(d) a filter removably mounted within said housing;

(e) a glass plate fixedly mounted within said housing between said filter and said ultraviolet radiation transmitting, light block element; and (f) conversion means for converting ultraviolet radiation at a first wavelength to ultraviolet radiation at a second wavelength, said conversion assembly comprising a supporting frame and a phosphor coated mesh substrate supported by said frame.

17. The apparatus as defined in claim 16 in which said mesh substrate is constructed from metal.

18. The apparatus as defined in claim 16 in which said mesh substrate is constructed from plastic.

19. The apparatus as defined in claim 16 in which said mesh substrate is constructed from glass.

20. The apparatus as defined in claim 16 in which said mesh substrate is constructed from quartz.

21. The conversion means as defined in claim 16 in which said phosphor on said phosphor-coated mesh substrate comprises a waveshift phosphor that will convert 254 nm ultraviolet radiation to 302 nm ultraviolet radiation.

22. The conversion means as defined in claim 16 in which said phosphor on said phosphor-coated mesh substrate comprises a waveshift phosphor that will convert 254 nm ultraviolet radiation to 365 nm ultraviolet radiation.

23. The conversion means as defined in claim 16 in which said phosphor on said phosphor-coated mesh substrate comprises a waveshift phosphor that will convert 254 nm ultraviolet radiation to both 302 nm and 365 nm ultraviolet radiation.

24. The conversion means as defined in claim 16 in which said phosphor on said phosphor-coated mesh substrate comprises a mixture of visible conversion spectra phosphors and ultraviolet phosphors.

* * * * *